United States Patent
Piron

(10) Patent No.: US 9,936,879 B2
(45) Date of Patent: Apr. 10, 2018

(54) METHOD, SYSTEM AND APPARATUS FOR ADAPTIVE IMAGE ACQUISITION

(71) Applicant: Cameron Anthony Piron, Toronto (CA)

(72) Inventor: Cameron Anthony Piron, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 0 days.

(21) Appl. No.: 15/513,379

(22) PCT Filed: Jan. 7, 2015

(86) PCT No.: PCT/CA2015/000011
§ 371 (c)(1),
(2) Date: Mar. 22, 2017

(87) PCT Pub. No.: WO2016/109876
PCT Pub. Date: Jul. 14, 2016

(65) Prior Publication Data
US 2017/0245761 A1 Aug. 31, 2017

(51) Int. Cl.
*A61B 5/00* (2006.01)
*A61B 34/20* (2016.01)
(Continued)

(52) U.S. Cl.
CPC .......... *A61B 5/0042* (2013.01); *A61B 5/0035* (2013.01); *A61B 5/055* (2013.01);
(Continued)

(58) Field of Classification Search
None
See application file for complete search history.

(56) References Cited

U.S. PATENT DOCUMENTS 6,487,303 B1* 11/2002 Yamaguchi ............... G06T 7/74
382/103
2003/0152275 A1* 8/2003 Chung .................... G06T 7/001
382/218
(Continued)

FOREIGN PATENT DOCUMENTS

EP    1942662 A1    7/2008
WO    2011134083 A1    11/2011

OTHER PUBLICATIONS

Examination Report dated May 10, 2017 for Canadian Patent Application No. 2959232.
International Preliminary Report on Patentability Report dated Jan. 30, 2017 for PCT International Application No. PCT/CA2015/000011.
(Continued)

*Primary Examiner* — Edward Park
(74) *Attorney, Agent, or Firm* — Perry + Currier Inc.

(57) ABSTRACT

A method of adaptive image acquisition includes obtaining a guide image of patient tissue; receiving an intraoperative image of a portion of the patient tissue from an imaging instrument; and storing the intraoperative image. The method includes comparing the intraoperative image with the guide image to identify at least one region of the guide image matching the intraoperative image; and determining whether the at least one region identified meets at least one accuracy criterion. When the at least one region meets the at least one accuracy criterion, the guide image is rendered with an indication of the at least one region on a display. When the at least one region does not meet the at least one accuracy criterion, the method includes receiving and storing a further intraoperative image; combining the further intraoperative image with the intraoperative image; and repeating the comparing and determining.

16 Claims, 8 Drawing Sheets

(51) Int. Cl.

| | | |
|---|---|---|
| *A61B 5/055* | (2006.01) | |
| *A61B 6/00* | (2006.01) | |
| *A61B 8/08* | (2006.01) | |
| *A61B 34/30* | (2016.01) | |
| *G06T 7/00* | (2017.01) | |
| *G06T 7/11* | (2017.01) | |
| *A61B 90/00* | (2016.01) | |

(52) U.S. Cl.
CPC ............ *A61B 6/501* (2013.01); *A61B 6/5235* (2013.01); *A61B 6/5247* (2013.01); *A61B 8/0808* (2013.01); *A61B 8/5246* (2013.01); *A61B 8/5261* (2013.01); *A61B 34/20* (2016.02); *A61B 34/30* (2016.02); *G06T 7/0014* (2013.01); *G06T 7/11* (2017.01); *A61B 2034/2057* (2016.02); *A61B 2034/2063* (2016.02); *A61B 2034/2065* (2016.02); *A61B 2034/302* (2016.02); *A61B 2090/3945* (2016.02)

(56) References Cited

U.S. PATENT DOCUMENTS

| | | |
|---|---|---|
| 2005/0027187 A1 | 2/2005 | Barth et al. |
| 2006/0165267 A1 | 7/2006 | Wyman et al. |
| 2011/0052033 A1 | 3/2011 | Shekhar et al. |
| 2014/0003700 A1* | 1/2014 | Hermosillo Valadez ............................ G06T 11/003 382/131 |
| 2014/0100449 A1 | 4/2014 | Begin et al. |
| 2014/0375822 A1* | 12/2014 | Jain .......................... A61B 5/06 348/187 |
| 2015/0139488 A1* | 5/2015 | Dharssi .................. G06Q 30/02 382/103 |

OTHER PUBLICATIONS

International Search Report dated Sep. 22, 2015 for International Application No. PCT/CA2015/000011.
Written Opinion dated Sep. 22, 2015 for International Application No. PCT/CA2015/000011.

* cited by examiner

METHOD, SYSTEM AND APPARATUS FOR ADAPTIVE IMAGE ACQUISITION

FIELD

The specification relates generally to medical image processing, and specifically to a method, system and apparatus for adaptive image acquisition.

BACKGROUND

Patient images such as preoperative MRI scans may be registered to surgical tracking systems to enable the tracking of surgical instruments and the registration of intraoperative images relative to the MRI scans. During surgical procedures, however, the registration between the preoperative images and the tracking system can become inaccurate, due to movement of the patient, deformation of tissue, shifting of tracking equipment, and the like.

Correcting an inaccurate registration traditionally requires a time-consuming interruption to the surgical procedure. The interruption may be omitted, but doing so introduces inaccuracies in image registrations, and may result in medical personnel being provided with incorrect information as to the location of surgical instruments such as imaging probes.

SUMMARY

According to an aspect of the specification, a method is provided, comprising: obtaining a guide image of patient tissue at a computing device; receiving an intraoperative image of a portion of the patient tissue at the computing device from an imaging instrument; storing the intraoperative image in a memory of the computing device; comparing the intraoperative image with the guide image to identify at least one region of the guide image matching the intraoperative image; determining whether the at least one region identified meets at least one accuracy criterion; when the at least one region meets the at least one accuracy criterion, rendering the guide image and an indication of the at least one region on a display; and when the at least one region does not meet the at least one accuracy criterion: receiving and storing a further intraoperative image; combining the further intraoperative image with the intraoperative image; and repeating the comparing and determining.

According to another aspect of the specification, a computing device for adaptive image acquisition is provided, comprising: a memory; a display; and a processor interconnected with the memory and the display, the processor configured to: obtain a guide image of patient tissue; receive an intraoperative image of a portion of the patient tissue from an imaging instrument; store the intraoperative image in the memory; compare the intraoperative image with the guide image to identify at least one region of the guide image matching the intraoperative image; determine whether the at least one region identified meets at least one accuracy criterion; when the at least one region meets the at least one accuracy criterion, render the guide image and an indication of the at least one region on the display; and when the at least one region does not meet the at least one accuracy criterion: receive and store a further intraoperative image; combine the further intraoperative image with the intraoperative image; and repeat the comparing and determining.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
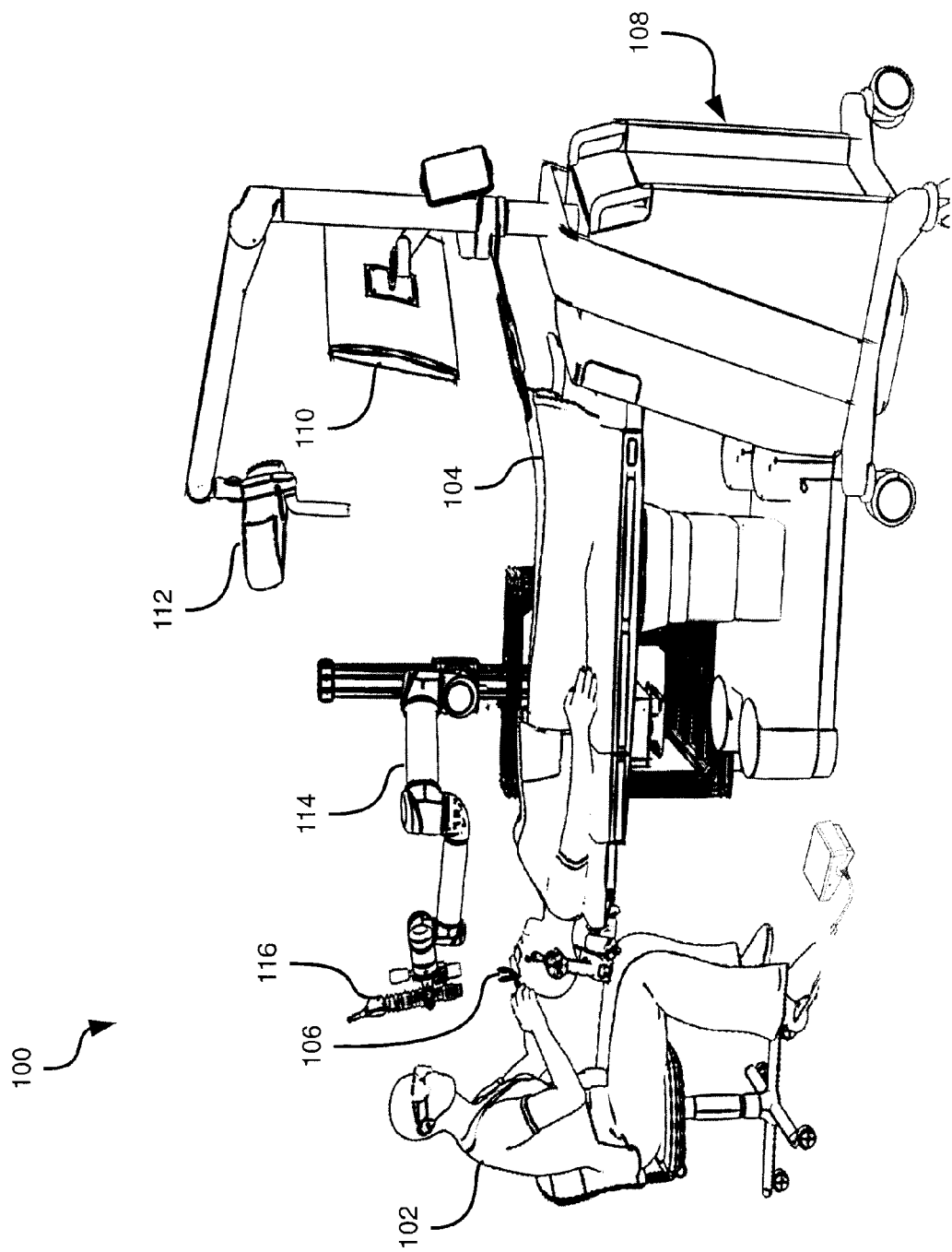
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 102, any of the above-mentioned surgical tools, or any combination thereof. Such markers, also referred to as fiducial markers, may also be mounted on patient 104, for example at various points on patient 104's head. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 102 by robotic arm 114, and may capture images of the brain of patient 104 for presentation on display 110. The movement of robotic arm 114 to place external scope 116 correctly over access port 102 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of patient 104's brain or portions thereof. Such preoperative images may be collected using any of a variety of imaging modalities, such as Magnetic Resonance Imaging (MRI), Optical Coherence Tomography (OCT), ultrasound, Computed Tomography (CT), optical spectroscopy and the like. For each of the above-mentioned imaging modalities, various imaging techniques may be used. Polarization Sensitive OCT and OCT elastography are exemplary uses of the OCT modality. Diffusion MRI (also referred to as diffusion tensor imaging, DTI) is an example use of the MRI modality. Raman spectroscopy is an example use of optical spectroscopy. A variety of other examples of the above modalities will also occur to those skilled in the art.

Preoperative images may be used for planning purposes. During the procedure, additional images (referred to as intraoperative images) may be collected of patient 104's brain, using any of the above-mentioned modalities.

In addition to being acquired with different imaging modalities, various preoperative images and intraoperative images may also be acquired at different resolutions. For example, an intraoperative ultrasound may provide data at a higher resolution over a smaller area or volume (e.g. by inserting an ultrasound probe within the brain of patient 104) than an external ultrasound could provide before the surgical procedure. Other imaging technologies may also be employed, as will be apparent to those skilled in the art. For example, beam forming techniques can be employed to focus a scan plane on a specific area of interest. Additional imaging technologies include adaptive MRI scanning, in which specific fields of view are interrogated as a subset of the overall volume.

As will be described in further detail below, the computing device housed in equipment tower 108 can perform various actions to register images taken of a certain area or volume of patient 104 with images of a larger area or volume of patient 104. In some embodiments, the "small-area" images are captured by, for example, a probe or other instrument employed intraoperatively.

The registration of images captured by the probe to a larger image thus identifies the current location of the probe relative to the larger image. The computing device is also configured to refine estimates of the probe's location using successive images captured by the probe, and to adaptively track the probe's location based on comparisons of images from the probe with the larger image.

Figure 2:
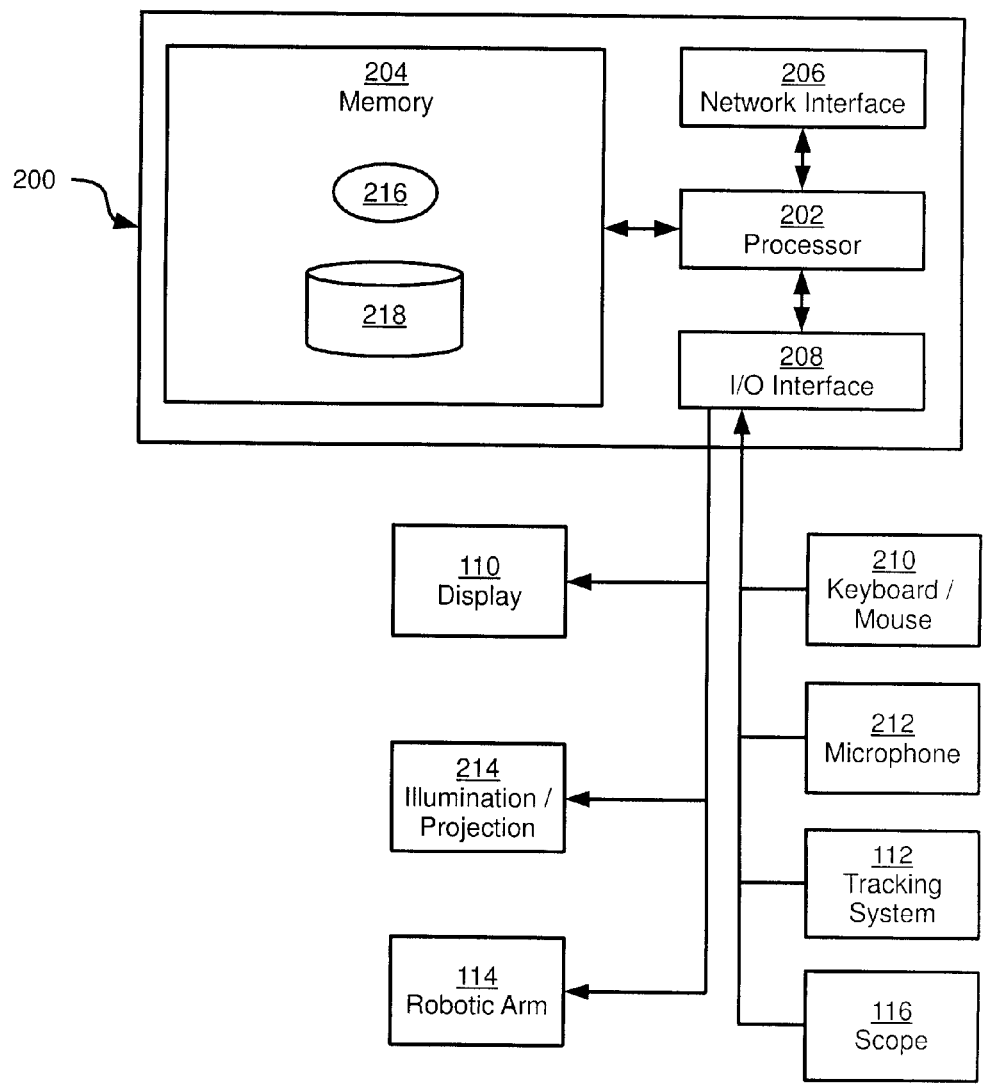
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 200. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, an adaptive image acquisition application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as MRI and CT scans, three-dimensional models of the brain of patient 104, and the like.

As mentioned above, computing device 200 is configured, via the execution of application 216 by processor 202, to perform various functions to register intraoperative images depicting certain areas of patient 104 with an image depicting a larger area of patient 104. Those functions will be described in further detail below.

Figure 3:
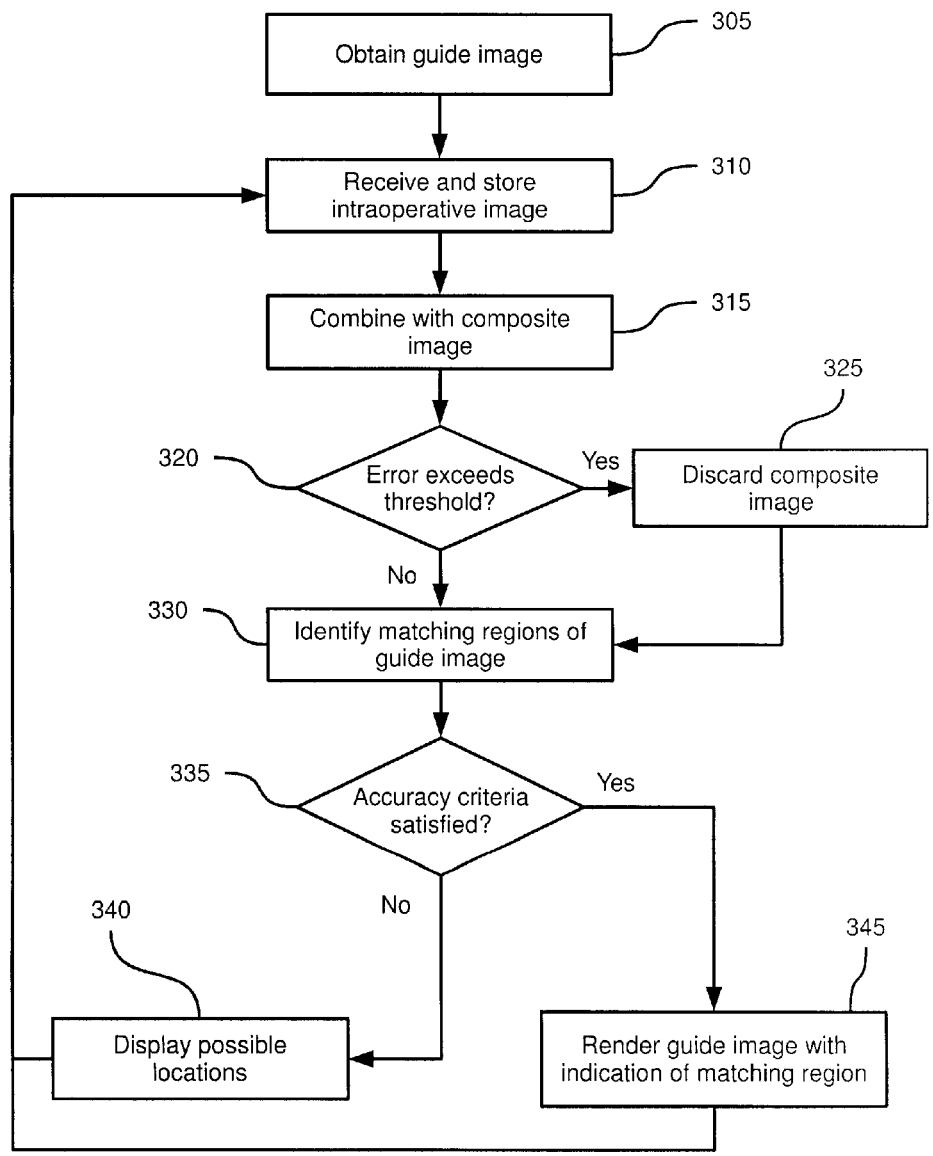
FIG. 3 depicts a method of adaptive image acquisition, according to a non-limiting embodiment.

Referring now to FIG. 3, a method 300 of adaptive image acquisition is depicted. Method 300 will be discussed in conjunction with its performance on computing device 200 as deployed in operating theatre 100. It will be apparent to those skilled in the art, however, that method 300 can also be implemented on other computing devices in other systems.

Figure 4:
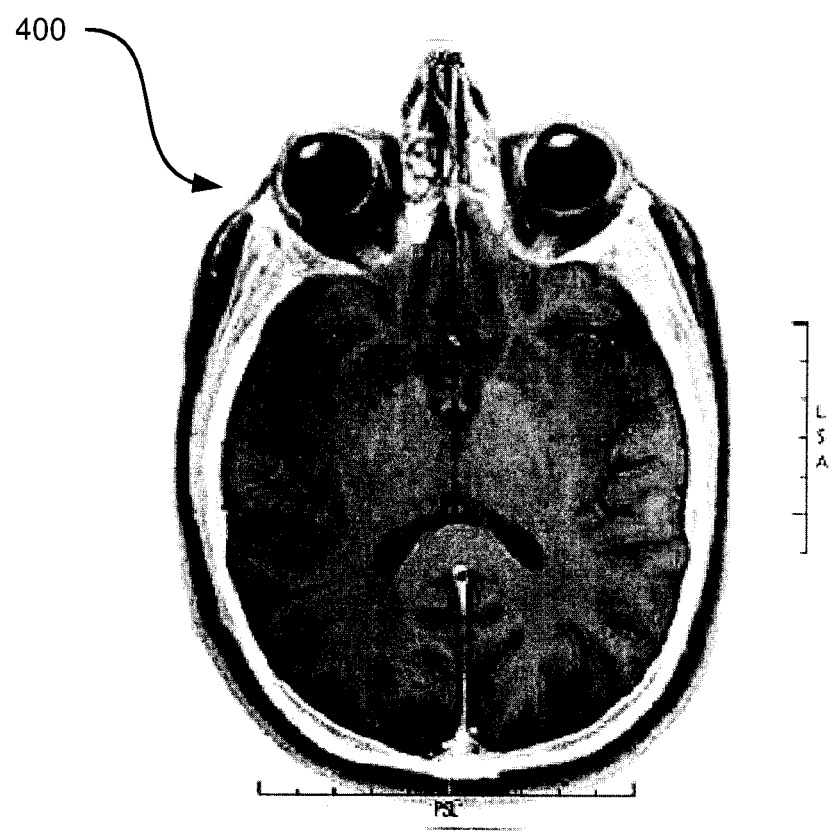
FIG. 4 depicts an example guide image from the method of FIG. 3, according to a non-limiting embodiment.

At block 305, computing device 200 is configured to obtain an image of at least a portion of patient 104 (in the present example, the image is of patient 104's brain). For example, the image may be the MRI scan 400 shown in FIG. 4. The image obtained at block 305 is referred to herein as the guide image, as subsequently captured intraoperative images are located within the guide image (that is, registered to the guide image) by computing device 200.

The guide image obtained at block 305 may be two-dimensional or three-dimensional, and can be an image captured preoperatively, or intraoperatively. Further, the method of acquisition of the guide image is not particularly limited. For example, computing device 200 may be connected directly to an MRI scanner (not shown), and receive data from the MRI scanner during the scan. In other examples, computing device 200 may receive the guide image from another computing device via network interface 206. The guide image is stored in memory 204, particularly in patient data repository 218. The preoperative image can contain or be associated with data describing the physical size of the area of patient 104 that was imaged. Such data can appear in the form of a resolution, dimensions, and the like.

In some embodiments, the guide image obtained at block 305 can also be registered to an atlas, such as a standard atlas associated with the particular area of patient 104 being imaged, or an atlas specific to patient 104.

At block 310, computing device 200 is configured to receive an intraoperative image of a portion of the patient tissue depicted in the guide image, and to store the intraoperative image in the memory 204. The intraoperative image received at block 310 is received from an imaging instrument, via I/O interface 208 or network interface 206. A variety of imaging instruments may provide the intraoperative image to computing device 200. For example, the intraoperative image can be received at computing device 200 from scope 116.

Figure 5:
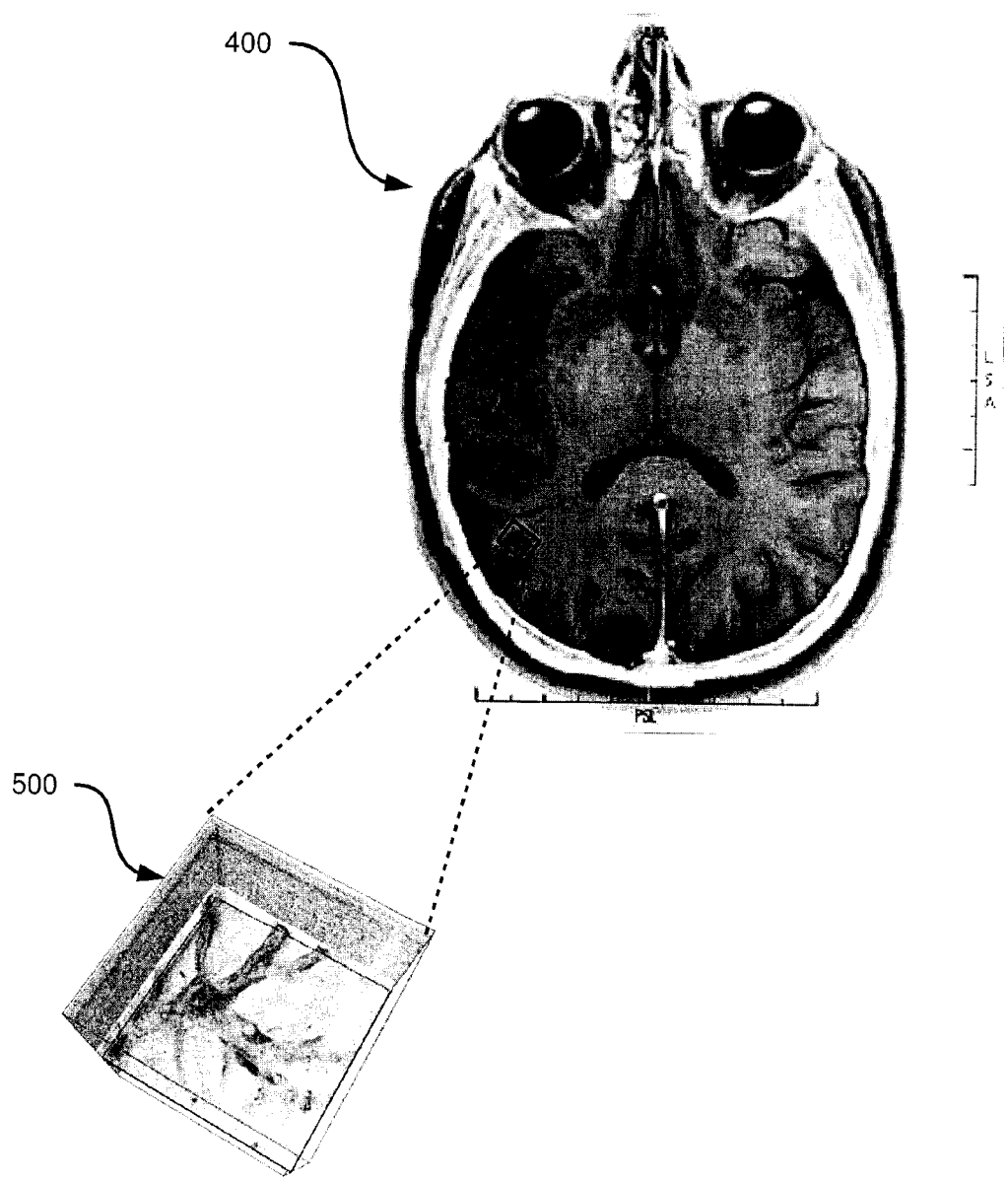
FIG. 5 depicts the guide image of FIG. 4 and an example intraoperative image from the method of FIG. 3, according to a non-limiting embodiment.

The nature of the intraoperative image is not particularly limited. The intraoperative image can be captured using the same modality as the guide image, or a different modality than the guide image. In general, the intraoperative image depicts a subset of the patient tissue depicted in the guide image, possibly at a higher resolution than the guide image. In other words, the intraoperative image can be a more detailed image of a part of the tissue depicted in the guide image. Turning to FIG. 5, an example intraoperative image 500 is shown in relation to guide image 400. As seen in FIG.

5, intraoperative image 500 provides a higher-resolution depiction of a portion of the tissue depicted in image 400.

Returning to FIG. 3, at block 315 computing device 200 is configured to combine the intraoperative image received at block 310 with a composite intraoperative image stored in memory 204, when such a composite image exists. In other words, the intraoperative image can be registered with a previously stored intraoperative image (including a combination of previous intraoperative images) using any suitable image registration technique, such as Applicant's co-pending PCT application no. PCT/CA2014/000849, filed Nov. 27, 2014 and entitled "Method, System and Apparatus for Quantitative Surgical Image Registration" which is herein incorporated by reference. At blocks 320 and 325, computing device 200 is configured to determine whether an error associated with the combination of the intraoperative image with the composite image exceeds a predefined threshold. If the error does exceed the threshold, computing device 200 can discard the composite image and begin building a new composite image, starting with the intraoperative image received at block 310.

As will be seen below, intraoperative images can be received in streams from imaging instruments as the imaging instruments are manipulated during the surgical procedure, and the performance of method 300 may be repeated, in some embodiments many times per second. Thus, the performance of blocks 315, 320 and 325 begins with an assumption that the intraoperative image received at block 310 depicts an area of patient 104 overlapping with the previous intraoperative image. If the overlap is poor or unidentifiable, the error computed at block 320 will be elevated and computing device 200 can determine that the above-mentioned assumption was incorrect, and that the imaging instrument may have moved suddenly to a different location.

In the present example performance of method 300, it is assumed that no composite image exists yet, and thus no error determination is necessary at block 320. The performance of blocks 320 and 325 will be discussed in further detail below in connection with repeated performances of portions of method 300. In the present example, however, the performance of method 300 proceeds to block 330.

The location of the tissues depicted by intraoperative image 500 within guide image 400 may not be known to computing device 200 or its operators (e.g. surgeon 102). Therefore, if the surgical procedure requires the location of a particular structure within the patient 104's brain, it may not be known whether the imaging instrument that provided the intraoperative image at block 310 is accurately positioned over the targeted anatomical structure. Computing device 200 is therefore generally configured to register the intraoperative image with the guide image in order to illustrate the location at which the intraoperative image was captured in the context of the guide image.

More specifically, computing device 200 is configured, at block 330, to compare intraoperative image 500 with guide image 400 to identify at least one region of guide image 400 that matches intraoperative image 500. The identification of matching regions within guide image 400 can be carried out according to any conventional image registration technique. For example, computing device 200 can be configured to identify features (such as edges, lines, points, a histogram of pixel intensities, and the like) of intraoperative image 500, and to identify regions of guide image 400 depicting the same area or volume of tissue as intraoperative image 500 (that is, accounting for differences in resolution between the images) that have similar features. Computing device 200 can be configured to identify possible matches to the intraoperative image in the guide image by computing error measurements for each possible match, and discarding those falling below a predefined threshold. In some examples, the elimination of certain matches as discussed above may be omitted, since block 335 provides a further opportunity to discard inaccurate matches.

In addition to, or instead of, the above-mentioned image features used in registration between intraoperative image 500 (or a composite of intraoperative images) and guide image 400, computing device 200 can be configured to generate a network model of any vessels (e.g. neurons) depicted in intraoperative image 500. For example, computing device 200 can be configured to detect such vessels and generate one or more metrics describing the detected vessels. The metrics can include vessel dimensions (e.g. length, diameter), a number of branches connected to each vessel, the relative locations along the length of the connections, and so on. An example of this technique, as applied to neurons, is described in Binzegger et al., Axons in Cat Visual Cortex are Topologically Self-Similar, *Cerebral Cortex*, February 2005, 15:152-165. The above metrics can be combined into dendrograms, in some embodiments. One or more dendrograms can also be constructed by computing device 200 for guide image 400, and the registration process can include comparison of the dendrograms. Other metrics that may be used in registration include fractal dimension and the like. The above-mentioned use of vessel-related metrics may be less susceptible to error introduced by tissue deformation than other image registration techniques.

At block 335, computing device is configured to determine whether the matching regions identified at block 330 meet at least one predefined accuracy criterion stored in memory 204. For example, turning to FIG. 6, another example intraoperative image 600 is depicted, along with three regions 604, 608 and 612 of guide image 400 identified by computing device 200 at block 330. Each of the regions 604, 608 and 612 are bounded by boxes illustrating the regions detected as possible matches to intraoperative image 600. Portions of guide image 400 beyond the boxes are also depicted, illustrating that the three regions depict different anatomical structures (although the bounded portions have similar appearances).

The criteria evaluated at block 335 may be defined in a variety of ways. In some embodiments, the criteria can specify a confidence level that must be exceeded (or alternatively, an error level that cannot be exceeded), as well as a number of matching regions for which that confidence level must be exceeded. For example, the criteria can specify that a single matching region must be identified with a confidence level of at least 90% (e.g. of the features identified in intraoperative image 600, ninety percent of those features are present in the matching region). The failure to identify any regions with a high enough confidence value, or the identification of multiple regions with a high enough confidence value, would both result in negative determinations at block 335.

A variety of other criteria will also occur to those skilled in the art. In general, at block 335 computing device 200 evaluates the regions of guide image 400 identified at block 330 against criteria to determine whether any particular one of the identified regions is likely to be a correct match to the intraoperative image. In some embodiments, the identification of matching regions of guide image 400 can be preceded by an application to guide image 400 of a transformation to account for tissue deformation or movement. For example, the patient 104's brain may have shifted during the procedure, and as a result may no longer be aligned with guide image 400. Thus, guide image 400 can be manipulated to re-align with the actual position of the brain, in order to improve alignment between guide image 400 and the intraoperative images.

Referring again to FIG. 6, regions 604 and 608 may both have high confidence values, as both exhibit similar features to intraoperative image 600 (e.g. an elongated feature, which may be a nerve bundle, terminating in a fork but lacking the small off-shoots shown in intraoperative image 600). Region 612, however, may have a lower confidence value, as it lacks the fork and the elongated feature terminates too early.

Figure 6:
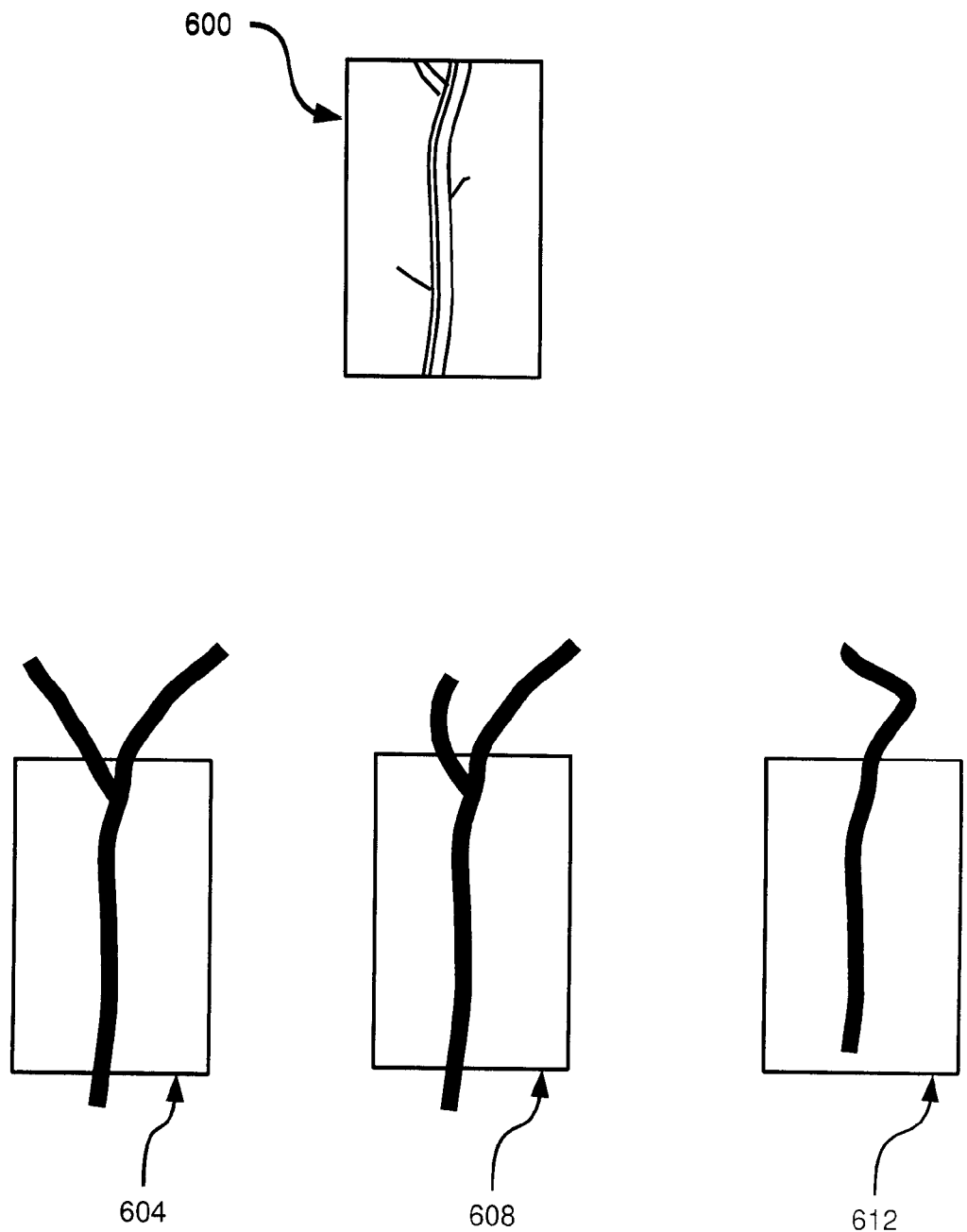
FIG. 6 depicts an intraoperative image and example matching regions of the guide image identified in the method of FIG. 3, according to a non-limiting embodiment.

The regions shown in FIG. 6 would result in a negative determination at block 335, because no single region exceeds the required confidence value (instead, both regions 604 and 608 exceed that value). In other words, intraoperative image 600 contains too little information to accurately locate intraoperative image within guide image 400. The performance of method 300 therefore returns to block 310. Prior to repeating the performance of block 310, computing device 200 can be configured, at block 340, to render guide image 400 on display 110, with indications of the regions identified at block 330. The interface presented on display 110 can include an alert that the regions shown did not satisfy the criteria at block 335 and may therefore be unreliable. Such an alert can include colour-coding, textual information, and the like. For example, a region presented on display 110 at block 340 can be overlaid on guide image 400 at each of the possible matching locations. The region may be presented in a manner distinct from a successful match, such as in a specific colour (e.g. red), flashing, or both.

Figure 7:
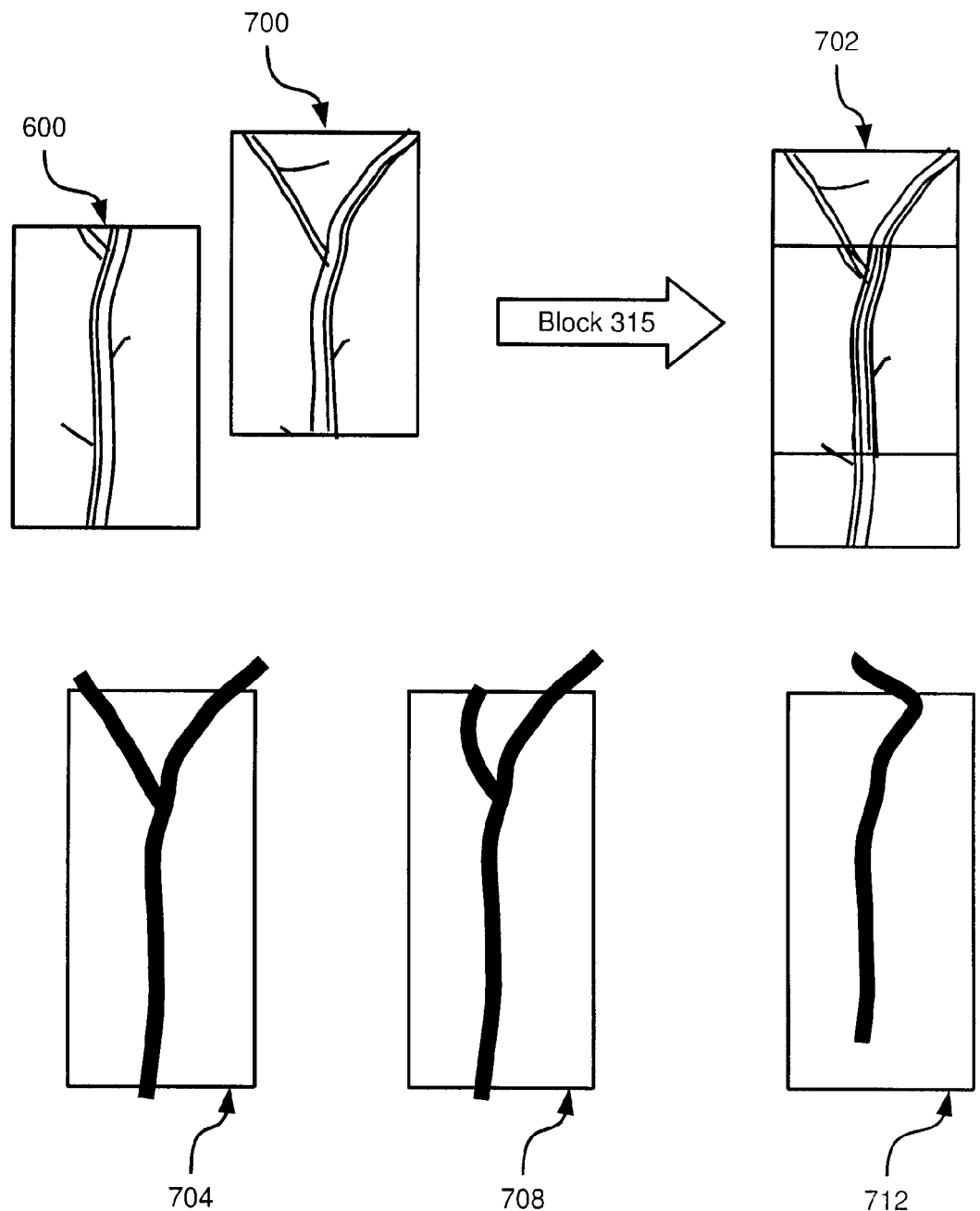
FIG. 7 depicts the intraoperative image of FIG. 6 in combination with a further intraoperative image, and example matching regions of the guide image identified in the method of FIG. 3, according to a non-limiting embodiment.

Returning to block 310, computing device 200 is configured to receive and store a further intraoperative image. FIG. 7 depicts intraoperative image 600, and a further intraoperative image 700, captured by moving the imaging instrument to a location adjacent to the location at which intraoperative image 600 was captured. At block 315, computing device 200 is configured to combine intraoperative image 700 with intraoperative image 600 to produce a composite image 702, shown in FIG. 7. As seen in FIG. 7, composite image 702 aligns matching portions of intraoperative images 600 and 700, and reveals that the two intraoperative images depict different, but overlapping, portions of an anatomical structure such as a nerve bundle. In other examples, if the accuracy of the match between intraoperative images 600 and 700 resulted in an error measurement that exceeded a threshold, the determination at block 320 would be negative and intraoperative image 600 would be discarded. Computing device 200 would then proceed solely with intraoperative image 700.

Computing device 200 is then configured to repeat the determination at block 330. Also shown in FIG. 7 are three regions 704, 708 and 712 corresponding to the anatomical structures shown in regions 604, 608 and 612 respectively. However, regions 704, 708 and 712 are enlarged in comparison with regions 604, 608 and 612 due to the greater size of composite image 702 relative to intraoperative image 600. From the enlarged regions shown in FIG. 7, it is clear that region 712 continues to be a poor match suffering from elevated error. Further, it is clear that region 708 is a less accurate match with image 702 than region 608 was with image 600. Region 704 remains an accurate match with image 702, and thus the determination at block 335 is affirmative (because a single region identified at block 330 exceeds a required level of confidence or concordance specified by the criteria).

Figure 8:
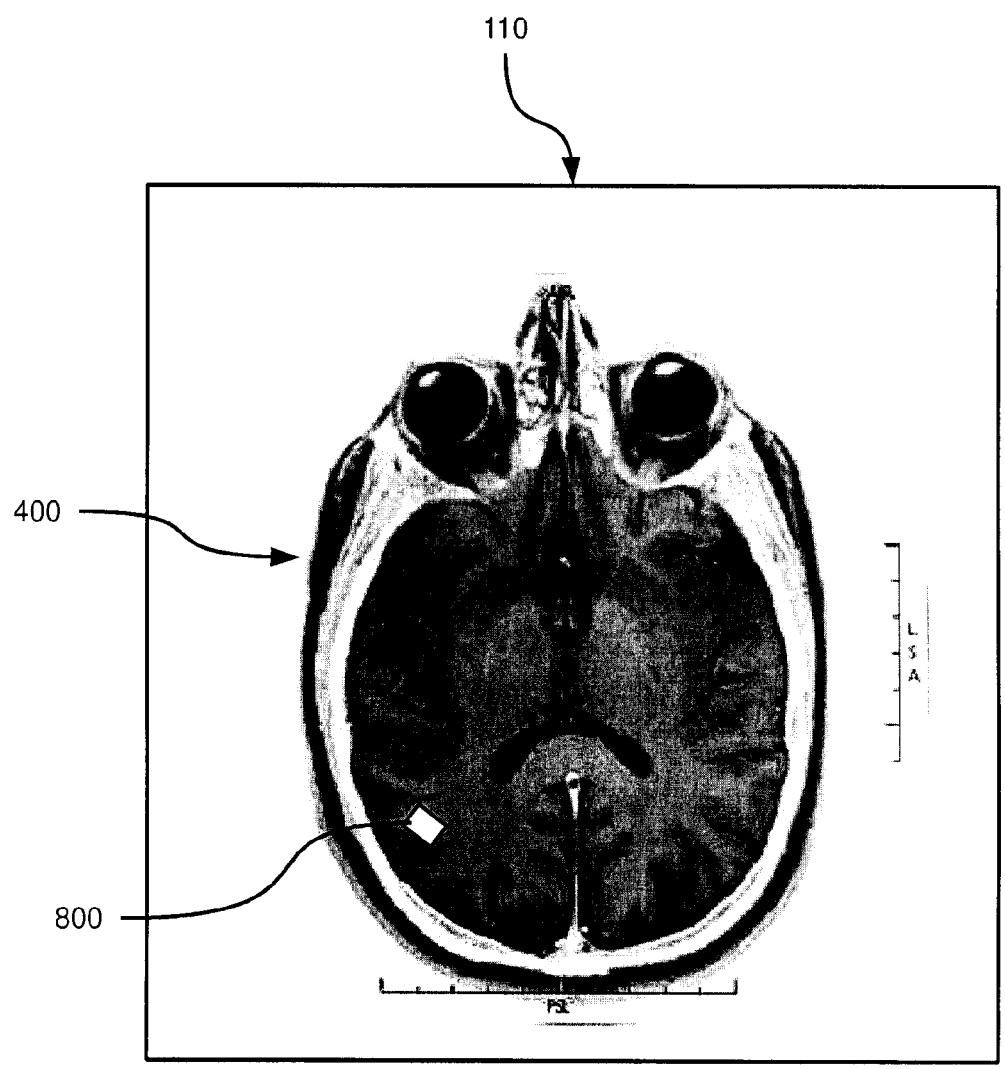
FIG. 8 depicts an interface rendered on the display of FIG. 1 following the performance of the method of FIG. 3, according to a non-limiting embodiment.

Following an affirmative determination at block 335, the performance of method 300 proceeds to block 345. At block 345, computing device 200 is configured to render guide image 400 on a display, such as display 110, with an indication of the matching region. Referring to FIG. 8, an exemplary interface is shown rendered on display 110, including guide image 400 and an indication 800 of the region of guide image 400 matching composite image 702. In other words, the interface shown in FIG. 8 displays the location from which the intraoperative images were captured. In other embodiments, composite image 702 itself may be superimposed on guide image 400 on display 110.

Following the performance of block 425, computing device 200 can return to block 310 to receive further intraoperative images. Thus, method 300 can be performed to continuously track the locations within patient 104 (as depicted in guide image 400) from which the intraoperative images are being captured. Older intraoperative images may be discarded as they lose concordance with the current intraoperative images (that is, as the imaging instrument moves away from the location where the earlier intraoperative images were captured).

Certain advantages to the embodiments discussed herein will now occur to those skilled in the art. For example, rather than interrupt a surgical procedure to capture an updated version of the guide image or re-register the guide image to tracking system 112, computing device 200 and method 300 provide for substantially continuous tracking of the location of an imaging instrument, without the need to track the motion of the instrument using tracking system 112.

Variations to the methods and systems described above are contemplated. For example, although the imaging instrument referred to above need not be tracked by tracking system 112, computing device 200 can receive an estimated position of the imaging instrument from tracking system 112 at block 330, to reduce the area of guide image 400 to be searched for matching regions.

In other variations, as mentioned earlier, intraoperative images can be captured using different modalities, and registered with each other through, for example, quantitative registration techniques such as those described in the co-pending PCT application no. PCT/CA2014/000849, filed Nov. 27, 2014 and entitled "Method, System and Apparatus for Quantitative Surgical Image Registration".

In further variations, the above methods and systems can be applied to tissues other than brain. For example, the vessel-based registration metrics mentioned earlier can be applied to guide images and intraoperative images of any tissue containing identifiable vessels. Such tissues include blood vessels, fascia, nerves, lymph vessels, and the like.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

I claim:

1. A method of adaptive image acquisition, comprising:
   obtaining a guide image of patient tissue at a computing device;
   receiving an intraoperative image of a portion of the patient tissue at the computing device from an imaging instrument;
   storing the intraoperative image in a memory of the computing device;

comparing the intraoperative image with the guide image to identify at least one region of the guide image matching the intraoperative image;

determining whether the at least one region identified meets at least one accuracy criterion including:
  (i) a minimum confidence level corresponding to a degree of matching between the at least one region and the intraoperative image; and
  (ii) a required number of regions meeting the minimum confidence level;

when the at least one region meets the at least one accuracy criterion, rendering the guide image and an indication of the at least one region on a display; and when the at least one region does not meet the at least one accuracy criterion:
  receiving and storing a further intraoperative image;
  combining the further intraoperative image with the intraoperative image to generate a composite image; and
  repeating the comparing and determining.

2. The method of claim 1, wherein the guide image comprises a preoperative image of the patient tissue.

3. The method of claim 1, wherein the minimum confidence level is defined as a maximum error threshold.

4. The method of claim 3, wherein the required number of regions is defined as a maximum threshold number of regions.

5. The method of claim 1, wherein comparing the intraoperative image with the guide image comprises:
  identifying a plurality of regions;
  determining an error value for each of the plurality of regions representing the accuracy of the match between each region and the intraoperative image; and
  discarding a subset of the plurality of regions having error values that exceed a threshold.

6. The method of claim 1, further comprising:
  prior to repeating the comparing and determining, determining an error level for the combination of the intraoperative image and the further intraoperative image;
  when the error level exceeds a predefined threshold, discarding the intraoperative image and repeating the comparing and determining based on the further intraoperative image; and
  when the error level does not exceed the predefined threshold, repeating the comparing and determined based on the composite image.

7. The method of claim 1, further comprising:
  when the at least one region does not meet the at least one accuracy criterion, prior to receiving and storing the further intraoperative image, rendering the guide image and an indication of the at least one region on the display.

8. The method of claim 7, further comprising:
  rendering an alert that the at least one region does not meet the at least one accuracy criterion on the display in association with the indication.

9. A computing device for adaptive image acquisition, comprising:
  a memory;
  a display; and
  a processor interconnected with the memory and the display, the processor configured to:
    obtain a guide image of patient tissue;
    receive an intraoperative image of a portion of the patient tissue from an imaging instrument;
    store the intraoperative image in the memory;
    compare the intraoperative image with the guide image to identify at least one region of the guide image matching the intraoperative image;
    determine whether the at least one region identified meets at least one accuracy criterion including:
      (i) a minimum confidence level corresponding to a degree of matching between the at least one region and the intraoperative image; and
      (ii) a required number of regions meeting the minimum confidence level;
    when the at least one region meets the at least one accuracy criterion, render the guide image and an indication of the at least one region on the display; and
    when the at least one region does not meet the at least one accuracy criterion:
      receive and store a further intraoperative image;
      combine the further intraoperative image with the intraoperative image to generate a composite image; and
      repeat the comparing and determining.

10. The computing device of claim 9, wherein the guide image comprises a preoperative image of the patient tissue.

11. The computing device of claim 9, wherein the minimum confidence level is defined as a maximum error threshold.

12. The computing device of claim 11, wherein the required number of regions is defined as a maximum threshold number of regions.

13. The computing device of claim 9, the processor further configured to compare the intraoperative image with the guide image by:
  identifying a plurality of regions;
  determining an error value for each of the plurality of regions representing the accuracy of the match between each region and the intraoperative image; and
  discarding a subset of the plurality of regions having error values that exceed a threshold.

14. The computing device of claim 9, the processor further configured to:
  prior to repeating the comparing and determining, determine an error level for the combination of the intraoperative image and the further intraoperative image;
  when the error level exceeds a predefined threshold, discard the intraoperative image and repeat the comparing and determining based on the further intraoperative image; and
  when the error level does not exceed the predefined threshold, repeat the comparing and determined based on the composite image.

15. The computing device of claim 9, the processor further configured to:
  when the at least one region does not meet the at least one accuracy criterion, prior to receiving and storing the further intraoperative image, render the guide image and an indication of the at least one region on the display.

16. The computing device of claim 15, the processor further configured to:
  render an alert that the at least one region does not meet the at least one accuracy criterion on the display in association with the indication.

* * * * *